United States Patent [19]

Mekker et al.

[11] Patent Number: 4,727,564
[45] Date of Patent: Feb. 23, 1988

[54] PORTABLE FIELD X-RAY DIAGNOSTIC SYSTEM

[75] Inventors: James G. Mekker, South Euclid; Joseph S. Deucher, Lyndhurst; Bruce E. Lutheran, Euclid; Anthony D. Szpak, Parma, all of Ohio

[73] Assignee: Picker International, Inc., Cleveland, Ohio

[21] Appl. No.: 877,885

[22] Filed: Jun. 24, 1986

[51] Int. Cl.⁴ .................... H05G 1/02; G03B 42/02
[52] U.S. Cl. .................... 378/197; 378/176; 378/193; 378/195; 378/196; 378/198
[58] Field of Search ............ 378/193, 195, 196, 197, 378/198, 176, 177, 189, 167, 20, 179; 250/522.1

[56] References Cited

U.S. PATENT DOCUMENTS

| | | | |
|---|---|---|---|
| 2,049,271 | 7/1936 | Nelson | 378/196 |
| 2,076,246 | 4/1937 | Nelson | 378/196 |
| 2,508,449 | 5/1950 | Davis et al. | |
| 2,588,124 | 3/1952 | Kizaur | |
| 2,668,912 | 2/1954 | Goldfield et al. | 378/177 |
| 2,754,426 | 7/1956 | Schiring et al. | |
| 2,842,676 | 7/1958 | Schiring et al. | |
| 4,190,774 | 2/1980 | Marinkovich et al. | 378/176 |

OTHER PUBLICATIONS

Picker 100/100 Military Table–Federal Stock No. 6525-615-8100.
Picker M.U.S.T. Military Table–Federal Stock No. 6545-999-6449.
Xonics Military Table.
Picker (Germany) Military Table.
Picker (England) Military Table.

*Primary Examiner*—Carolyn E. Fields
*Assistant Examiner*—Joseph A. Hynds
*Attorney, Agent, or Firm*—Watts, Hoffmann, Fisher & Heinke Co.

[57] ABSTRACT

A compact, lightweight, portable, versatile and modular field x-ray system is disclosed. A base member is provided and supports an x-ray table. Two vertical masts are also coupled to the base, for movement alongside the table in a direction parallel to its longitudinal dimension. The masts move independently of one another but can also be linked together for movement in unison. A tube head is attached to one mast by articulated structure, including a series of offset arms, which affords the tube head 6 degrees of freedom of movement, both above and below the x-ray table. A spot film device is movably coupled to the second mast. The second mast and spot film device are manually removable from the remainder of the system for operation in radiographic only mode. When the masts are linked together, the tube head, because of the offsetting nature of the coupling arms, can be precisely vertically aligned with respect to the spot film device, and the entire assembly of masts, tube head and spot film device can be moved in unison for fluoroscopic panning.

42 Claims, 19 Drawing Figures

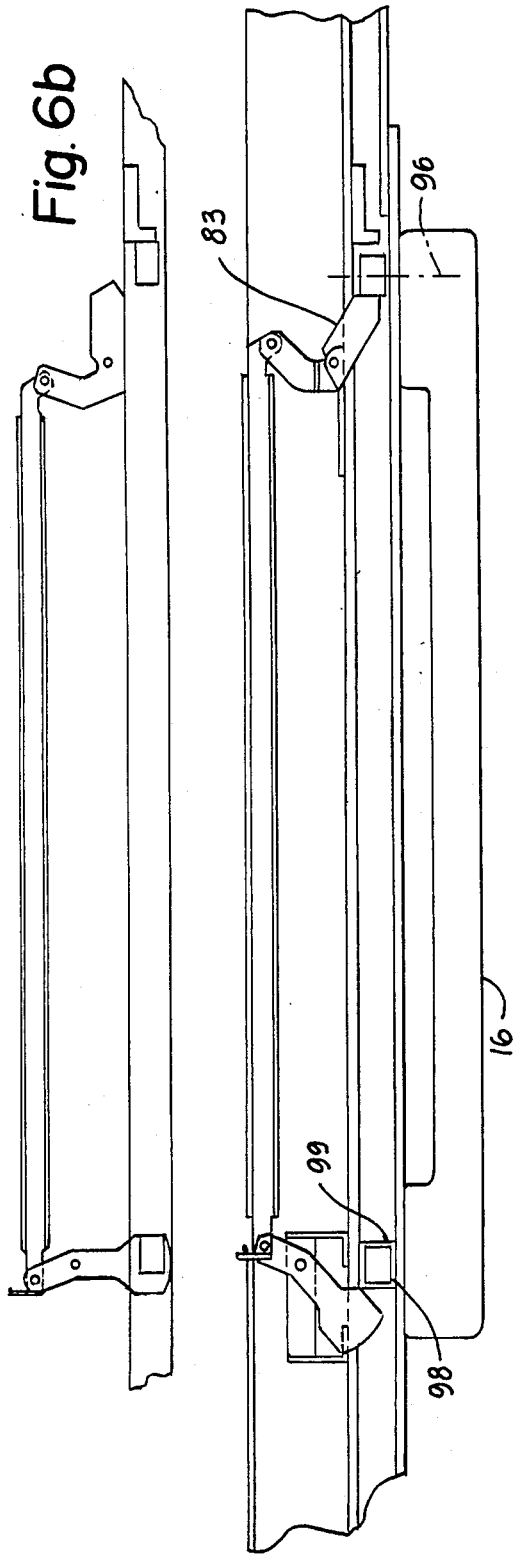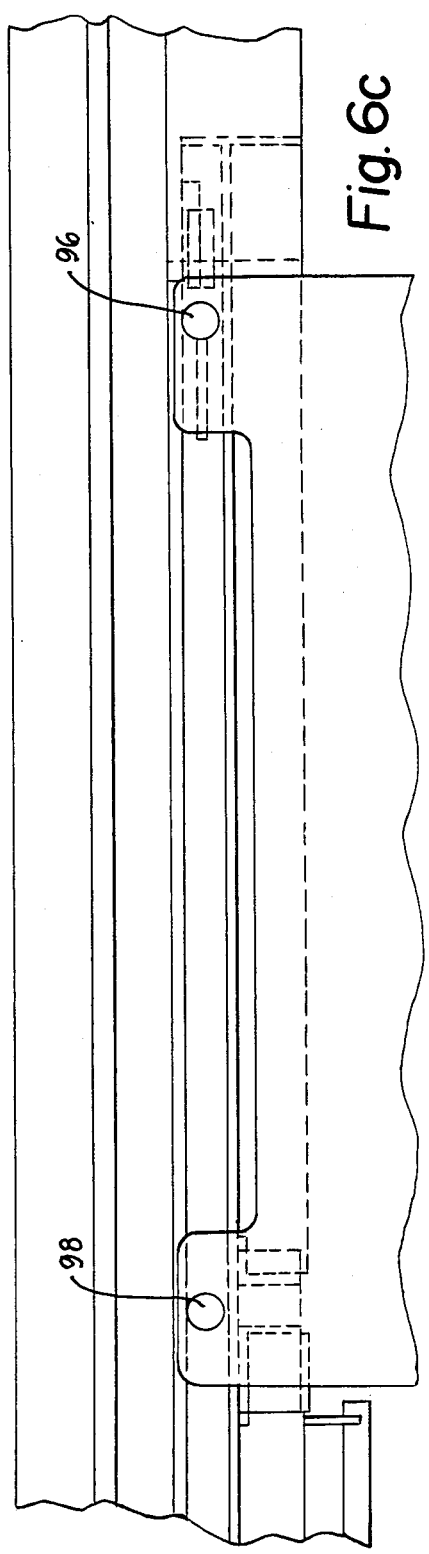

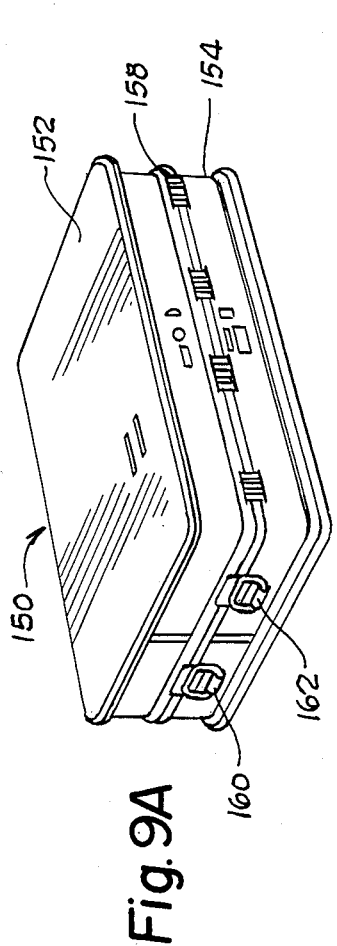
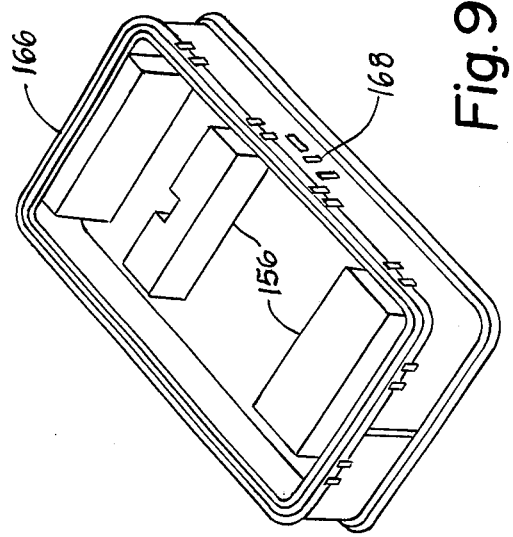
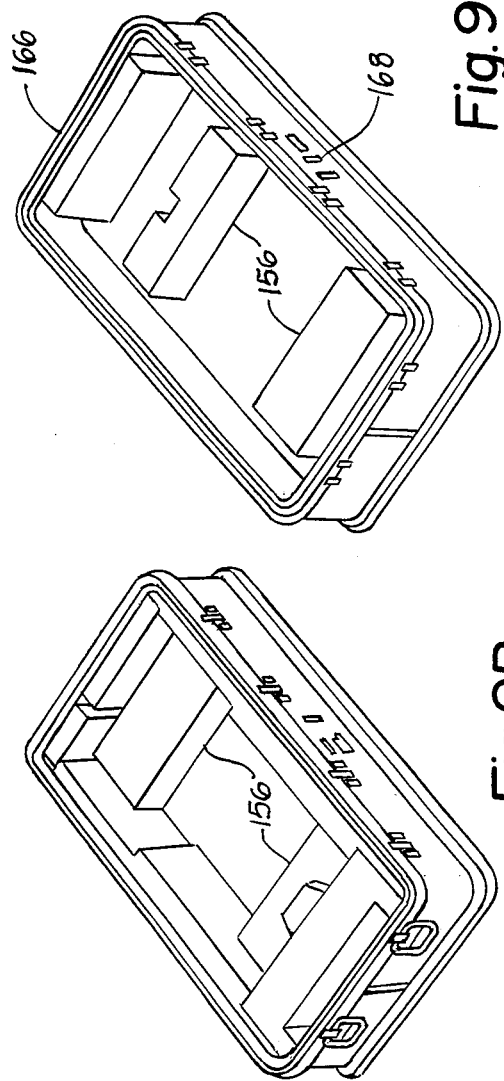

PORTABLE FIELD X-RAY DIAGNOSTIC SYSTEM

TECHNICAL FIELD

This invention relates to the field of medical diagnostics, and more particularly to a lightweight, compact, portable and versatile combination radiographic/fluoroscopic method and apparatus.

BACKGROUND ART

In a conventional radiography system, an x-ray source is caused to direct a divergent area beam of x-rays through a patient. A cassette containing an x-ray sensitive phosphor screen and film, sensitive to light and x-rays, is positioned in the x-ray path on the side of a patient opposite the source. Radiation passing through the patient's body is attenuated in varying degrees in accordance with the various types of tissue through which the x-rays pass. The attenuated x-rays from the patient emerge in a pattern, and strike the phosphor screen, which in turn exposes the film. The x-ray film is processed to yield a visible image which can be interpreted by a radiologist as defining internal body structure and/or condition of the patient.

Many operating mode geometries are used in radiography and fluoroscopy.

In some applications, the patient reclines on an x-ray table having a top surface through which x-rays can pass with little attenuation. The source is located above the table and projects x-rays downwardly through the patient's body. The table is equipped with means, often called a "bucky", for accommodating and holding in place a radiographic film cassette just below the surface of the table.

In other applications, the source is located beneath the table top and projects x-rays upwardly through the table top and through the patient's body. A filmer assembly, having means to accommodate and support a radiographic film cassette, is located above the patient's body and aligned in the beam. These two applications are often referred to generally as "horizontal" radiography.

In another application, known as vertical radiography, the patient stands upright and a source is positioned in front of his body to propagate radiation through it along a geneally horizontal path. The radiographic film cassette or a spot filmer is supported behind the patient and is exposed by the x-rays.

In another type of radiography, known as "lateral", the patient reclines on the table, and the source is positioned generally beside the table to propagate its x-ray beam transverse to the longitudinal dimension of the table and through the patient's body. The radiographic cassette is appropriately supported on the opposite side of the table to receive the x-rays passing through the patient's body.

Still other radiogrpahic techniques are known as "oblique" work, in which the source is tilted or angled about one or more axes with respect to the table top to propagate x-rays through a patient lying upon the table. In one so-called oblique mode, the x-ray source is suspended over the table, and is rotated to an oblique angle, with respect to the table top, about an axis which is substantially horizontal and is perpendicular to the longitudinal dimension of the table.

Another radiographic technique defined here as "off table work" is typically performed using ceiling mounted x-ray systems or floor to ceiling mounted systems.

In fluoroscopy, a real time substantially continuous image, rather than a snapshot, of the patient's internal body structure is produced. The source directs x-rays through the patient's body, which are received by a fluoro device located on the opposite side of the patient. The fluoro device includes known means for producing a continuous image of the emergent pattern of x-rays transmitted by the patient's body. In fluoroscopy, the x-ray source is operated at a lower output level than in radiography. The output in fluoroscopy, however, rather than being a single pulse, is continuous.

Known types of fluoro devices employ a scintillation screen which responds to the incident pattern of x-rays to produce a directly visible image. Other types of fluoroscopic devices employ an image intensifier tube, which receives the x-ray pattern at a relatively large input face, and produces at an output face a corresponding image whose brightness is substantially enhanced with respect to the brightness of a simple scintillation screen. Where an image tube is used, the output is often viewed by a television camera and displayed on a monitor.

In fluoroscopy, mode geometries include those discussed above in connection with radiography, except for lateral, oblique and off-table work.

It can be seen from the foregoing discussion that, in order to accomplish all the various modes of radiography and fluoroscopy, the source and detector, be it radiographic film, a filmer assembly, or a fluoro device, must be positionable in a large multiplicity of locations with respect to the x-ray table and to the patient's body. This situation is complicated where a system is needed having the capability of practicing imaging in both radiographic and fluoroscopic modes, because of the necessity to support and position not only the radiation source, but also a radiographic film cassette, a filmer assembly, a fluoro device, and the patient.

Prior art x-ray systems either do not have the capability and versatility for performing operations in all the modes discussed above, or they are quite complex, bulky, and heavy, and require a permanent or fixed installation, such as including supporting walls and ceilings. Such systems also require large floor area to achieve such versatility.

One type of prior art system employs an x-ray source mounted only for location under the x-ray table in conjunction with a fluoro device and a filmer mounted on the table. Such devices obviously suffer from the disadvantage that they cannot be adapted to operate to position the source both above and below the table.

Other systems attempt to deal with the disadvantages of such systems by employing two sources, a first located above the table, a second located beneath it. The first source, located above the table, is typically mounted on either a ceiling supported track, a wall mounted track, or other tower structure. In such instances, the second source, located below the table, is dedicated for undertable use exclusively, and the above-table source is dedicated for overtable work. Such systems cannot stand independently of the support means provided by a fixed wall or ceiling.

Most prior art systems provide at least some of the desired component movement by means of electromechanical servo systems driven by controllable electric motors. The requirement for these servo drives is a disadvantage where space, weight and reliability are considerations, or where electric power is not readily available.

While systems such as those described above have been found satisfactory for operation in permanent installations, such as in permanent doctors' offices and large hospitals, these systems are inordinately complex and bulky for convenient use in portable applications. Such portable applications can include portable x-ray equipment for transport to a scene of traumatic injury, such as for use in conjunction with domestic trauma treatment centers, and in transportable military hospitals and first aid stations.

In such applications, it is particularly desireable that all equipment be as simple and reliable as possible, since repair capability may be inaccessible in the field. The equipment should be able to withstand repeated assembly and knockdown for transport. It must be capable of being knocked down, preferably without tools, into relatively small components which can be carried by humans without the aid of mechanical lifting and transport equipment, such as where it would be desireable to load an x-ray system in pieces into a vehicle for quick transport to and reassembly at a site of need.

Needless to say, x-ray equipment designed for portable application must be sufficiently rugged to resist damage or maladjustment resulting from vibration and other shock which normally occurs during transport of field equipment.

Another problem inherent in portable x-ray equipment is that, often, the equipment is used where electric power is in limited supply and form. It is sometimes a problem to find sufficient electric power, or the needed frequency, phase and/or voltage, to actuate relatively heavy electromechanical components such as motors and other servo equipment used to drive prior art type radiographic equipment.

The requirements of radiographic equipment used for initial evaluation of extensive traumatic injury often differ somewhat from the requirements for radiographic equipment used in permanent installations. Often, in portable units such as military field hospitals, sometimes called "MASH", the most important requirement for a radiographic system is to be able to reliably scan large areas of the human body very quickly, convert rapidly from one operating mode to another, and to rapidly produce images of reasonable quality illustrating gross traumatic injury caused by shrapnel, bullets and the like. It is also important to be able to perform a variety of radiographic and fluoroscopic procedures with little or no patient movement.

One previous military system was constructed in modular manner to break down into subassemblies which could be individually loaded into reusable containers for transport. This system, dating back to pre-World War II, was known as the "50/90" system, manufactured by Picker Corporation, of Cleveland, Ohio, USA. Though the 50/90 system was satisfactory for some uses, it had several disadvantages. It had very limited provision for multiangle oblique radiographic operation. It had no spot filmer capability. Its fluoro was done with only a phosphor screen. In vertical radiography, the bucky could not be employed.

It is an object of this invention to provide a lightweight, rugged, compact, versatile, reliable, simple, easily disassembled radiographic/fluoroscopic system capable of executing a large variety of radiographic and fluoroscopic operational modes, and without the need for the application of electromechanical power to move system components.

DISCLOSURE OF INVENTION

The disadvantages of the prior art are reduced or eliminated by the use of a compact, lightweight, simple, versatile and portable x-ray system for examining patients. Such a system includes a base and an x-ray table top defining a longitudinal dimension. Means is provided for supporting the x-ray table top above the base. The system includes first and second masts coupled to the base. An x-ray source is provided, along with means for coupling the source to the first mast. A fluoro device and/or a spot filmer assembly is coupled to the second mast.

In accordance with a more specific embodiment, the x-ray source is coupled to the mast by an articulated structure which supports the source for movement in 6 degrees of freedom.

More specifically, the articulated means includes a collar member mounted on the first mast, by way of vertical carriage member, for vertical motion up and down the first mast and additionally for rotative motion about a center line axis defined by the first mast. A first arm extends outwardly from the collar member. A second arm is mounted for pivotal movement with respect to the first arm about a substantially vertical axis. The second arm defines an axis generally extending along its longitudinal dimension.

Additional means is provided for coupling the x-ray source to the end of the second arm to facilitate the following movement of the source: rotative movement about an axis parallel to the second arm axis; rotative movement about an axis substantially horizontal and orthogonal to the second arm axis, and rotative movement about a vertical axis substantially orthogonal to the second arm axis.

One or both of the masts is coupled to the base by means which affords translational movement of the vertical masts along a horizontal path which is substantially parallel to the longitudinal dimension defined by the table top.

Additionally, when the articulated arm twin mast system is coupled with a table support and pivoting system whose pivot axis is located near the middle of the table length, the result is a substantial shortening of the required longitudinal length of the overall system while allowing clinically preferred relative orientations of patient, x-ray source table top and film. By contrast, in the above referenced 50/90 system, the X-ray tube could not be brought to the right of the table when vertically oriented without substantial system alteration. The center table pivot of the present invention, combined with the other movements provided, allow achievement, within a short longitudinal length, of a 40 inch S.I.D. in vertical radiographic mode as well as an acceptable S.I.D. in vertical fluoro mode. This nonobvious combination of a multiplicity of possible geometries forms a unique highly versatile compact system.

It can be seen from the above description that this system possesses unusual versatility in terms of being able to position the x-ray source above or below the table top, with a range of motion provided by the unique configuration of the slides, pivots and geometry of the entire system. This system is capable of conversion among horizontal table fluoro, horizontal table radiographic, horizontal table lateral, and horizontal table oblique, including Townes, modes of operation, all without removing the patient from the table. This is a very important feature in trauma centers.

Additional flexibility is provided by means which is employed to mount a filmer assembly and/or fluoro device on the second mast. A carriage with a collar member mounted on the second mast affords vertical movement up and down the mast and rotational capability for orbiting about an axis defined by the second mast. Additional means is provided for pivoting the fluoro device/filmer assembly for rotative motion about a substantially horizontal axis which is perpendicular to the axis of the second mast.

In instances in which both masts are translatable along one or more horizontal paths parallel to the table top longitudinal dimension, means is provided for selectively linking the masts together for movement in unison along their respective path or paths. Such a capability is useful in instances in which the system is operating in a fluoroscopic mode, and it is desired to move, or "pan" the fluoro system relatively over various portions of the patient's body, while maintaining source to film alignment.

There is a minimum center-to-center spacing between the two movable masts, since they cannot both occupy the same space. The offset nature of the tube mounting to the first mast, by way of the arm structure, enables the precise vertical alignment of the x-ray source, mounted on the first mast, with the fluoro device, mounted on the second mast, notwithstanding that the masts themselves cannot be moved to the same longitudinal location with respect to the table top.

Additional flexibility is provided by means for mounting the table for various movements. The table is mounted for translational movement, when horizontal, in directions both parallel and perpendicular to its longitudinal dimension. Additionally, the table is mounted to switch between horizontal and vertical modes by translate and pivot apparatus for affording rotative movement of the table about a horizontal axis near the table center and perpendicular to its longitudinal axis. The table must be translated before being tilted, causing it to end up, after rotation in the middle of the base.

Importantly, the unique combination of offset in the x-ray tube support arm which is designed to permit movement of the tube offset either to the left or right of its support mast combined with a table tilt pivot position located in the central region (rather than at the end) of the table top results in a system where the effective movement of the x-ray tube is very extensive without the necessity for employing a long longitudinal track system. This permits achievement of a 40 inch S.I.D. in vertical radiographic work, as well as vertical fluoroscopic work with adequate S.I.D. while still maintaining a short overall system length.

The unique configuration of twin mast and offset tube support arm and centrally positioned table also permits the achievement of a system that is extremely well suited to conversion to a radiographic only system by simply removing the fluoroscopic device, spotfilmer and its associate vertical support mast and longitudinal carriage. What remains is a highly flexible compact radiographic system having capability to do radiographic work in lateral, overtable and oblique Townes modes with the table top horizontal, with the cassette carrying device located behind the patient and under PBC control. It also has the capability to do vertical table radiographic procedures in both normal and oblique directions with the cassette carrying device located behind the patient and under PBL control.

To accomplish the total versatility of this sytem, the current state of the prior art typically utilizes an auxiliary ceiling, mounted, or floor to ceiling track mounted, x-ray source in addition to a table with x-ray source mounted below it.

The system also incorporates hand operable locking and braking means for fixing, when desired, the relative orientations of the various components among one another. Some brakes and locks are normally electrically actuated, but can be manually overridden. No lead counterweighting is used in the system. No elements are provided whose sole function is counterweighting. Due to the light weight and simplicity of the system, no means is required for providing mechanical advantage for executing operator induced component movement. Rather, all movement can be accomplished by direct application of manual applications of force by an operator on the components whose movement is desired.

The offset in the x-ray tube support arm is uniquely configured to also place the tube in line with the spot filmer when performing horizontal fluoroscopic procedures.

Other aspects of the present invention will be appreciated from a reading of the following detailed description and from the drawings, in which:

BRIEF DESCRIPTION OF DRAWINGS

FIGS. 9A–9C are isometric drawings illustrating a manner of knocked down and storage for transport of a system in accordance with a system of the present invention;

BEST MODE FOR CARRYING OUT THE INVENTION

Figure 1:
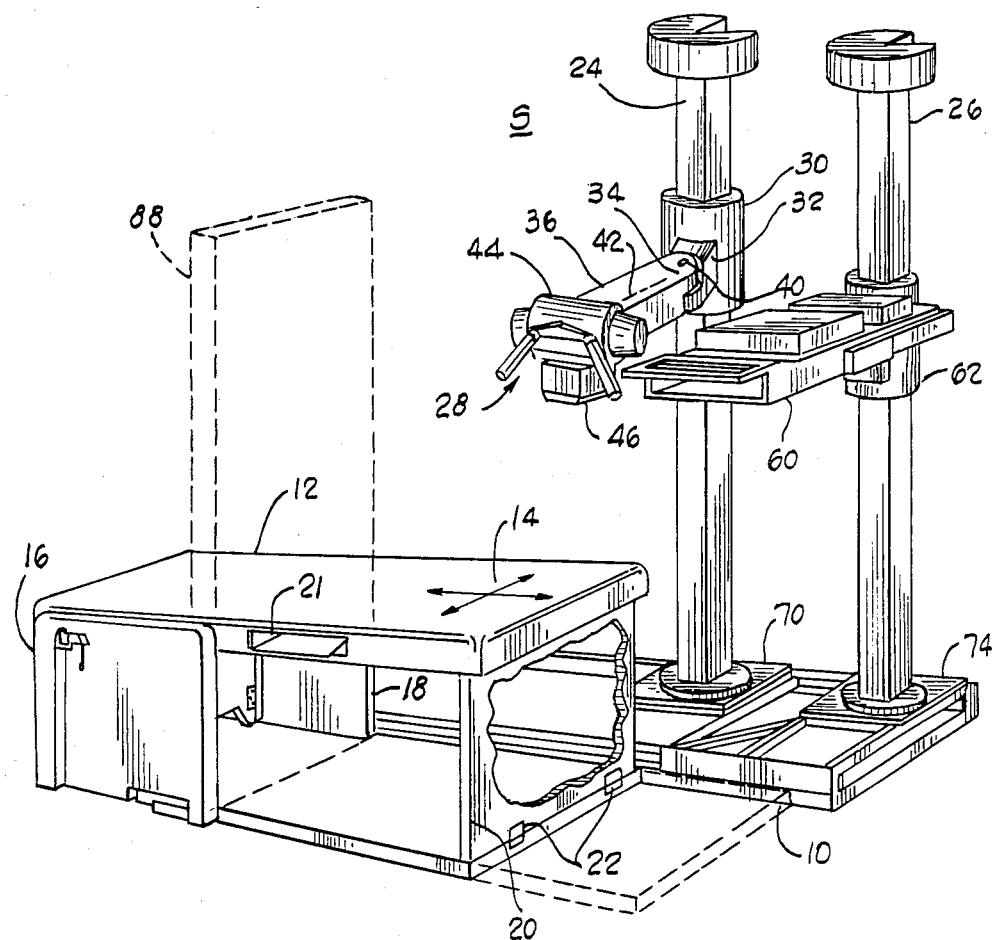
FIG. 1 is an isometric drawing of a system embodying the present invention.
Figure 2:
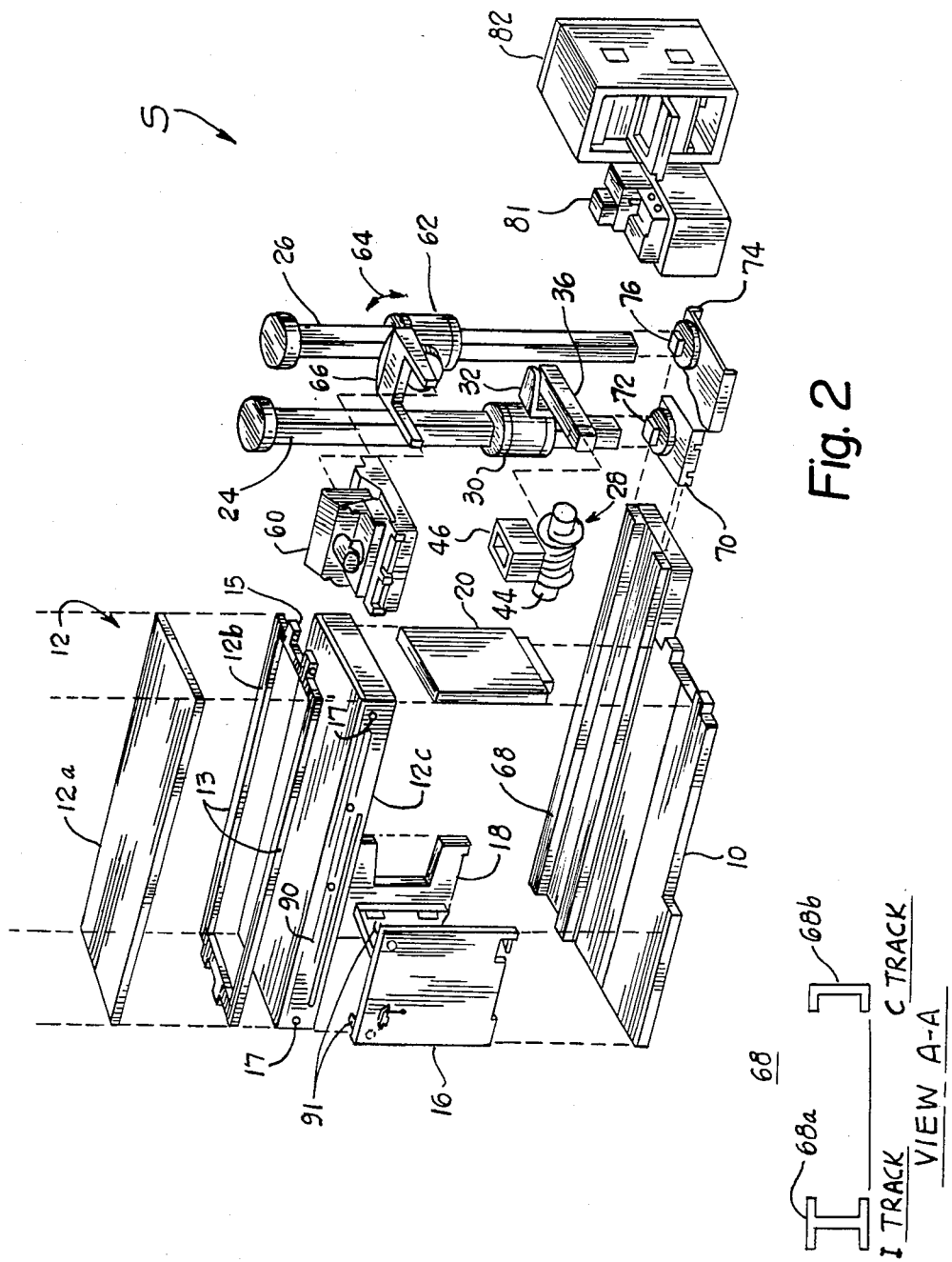
FIG. 2 is an exploded overall view of a system embodying the present invention.

FIGS. 1 and 2 illustrate in overall fashion an embodiment of a system S for carrying out the present invention. The system includes a base 10 which accommodates the mounting thereon of the other components of the system, and defines generally a small "footprint" or area occupied by the system S. The base 10 is made of an aluminum honeycomb material. The base 10 comprises several segments which are hinged together for folding into a more compact configuration for transport.

An x-ray table assembly 12 is shown whose function is to support a patient during x-ray examination. The table assembly includes a table top 12a, a subframe 12b, and a support tilt frame 12c, as shown in FIG. 2. The table top member 12a is elongated and defines a longitudinal dimension extending generally in the direction of one of the arrows 14 shown in FIG. 1.

The table top member 12a is an elongated portion of rigid material which is generally transmissive of x-rays. The table top member 12a is mounted for movement with respect to the subframe member 12b by longitudinal means of known roller bearing structure which rides in tracks 13 in the subframe member 12b.

The subframe member 12b is, in turn, movably mounted for transverse motion with respect to the support tilt frame 12c. A pair of bearing supports 15 are mounted on each end of the subframe member 12b. On one end, the bearing support members each define a hole having a horizontal axis perpendicular to the longitudinal axis of the table top member. The holes defined by one pair of bearing support blocks are coaxial and of the same size. The bearing support blocks accommodate in the holes a shaft (not shown), at one end of the subframe member which are attached at point 17' to the support tilt frame 12c. The shaft is also horizontally aligned perpendicular to the length of the table top. The other end utilizes cam follower type bearing members which ride in a C-shaped channel and are therefore tolerant of dimensional changes between the members 12b and 12c.

It can thus be seen that the table top member 12a is enabled to "float" in two directions of movement, defined by the arrows 14 in FIG. 1, i.e., longitudinally and transversely.

Figure 6A:
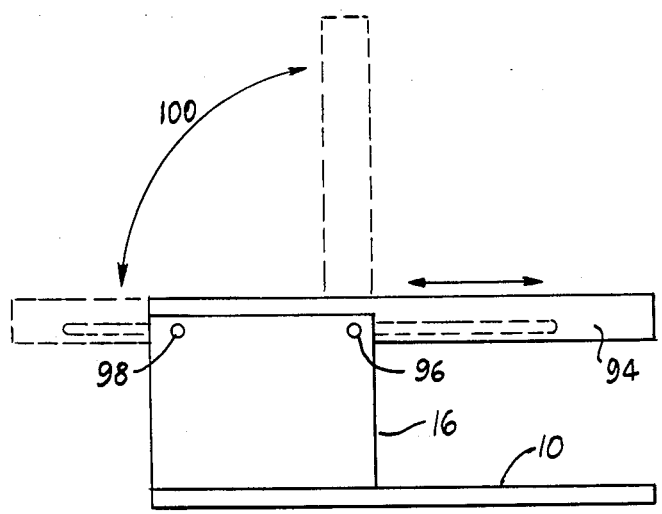
FIG. 6 is a front elevational view illustrating a portion of the system shown in FIGS. 1 and 2.

Additional provision is made for longitudinal movement of the entire table assembly. Slotted track structure 90 is provided in each side of the support tilt frame 12c. The track structure 90 is engaged in known fashion with roller bearings 91 in each of a pair of upright support panels 16, 18. In a manner described in more detail below, the sliding engagement of the support tilt frame 12c with the uprights 16, 18 permits the entire table assembly to be moved longitudinally. Table tilting is prevented unless the table assembly is moved a sufficient distance to the left as shown in FIGS. 2 and 6. When the table assembly is moved a sufficient distance to the left, the slot and track structure 90, and bearings 91, permits tilting rotation of the table top to a vertical position.

This selective tilting capability is enabled by known bearing capture and gate mechanism associated with the track structure 90, and bearing structural 91, which maintains the table assembly in a horizontal position until the table assembly is moved to a predetermined point on its longitudinal travel path, and the gate is actuated by an operator.

Referring to FIG. 1, the table assembly also incorporates a radiographic film cassette tray on its underside. The cassette tray 21 is adjustable in position longitudinally with respect to the table top member 12a and 12b.

Means is provided for supporting the table top member 12 above the base 10. The table top supporting means includes the pair of upright side panels 16, 18, and a right hand end panel 20. The right hand end panel 20 is hingedly coupled as at 22 to the base 10. This hinged coupling, as described in more detail below, enables the right hand end panel member 20, under appropriate circumstances, to be rotated downwardly in a clockwise direction as shown in FIG. 1 until it touches the surface upon which the base 10 rests. In this configuration, the right hand end panel 20 can thus be converted to form a ramp leading from the underlying surface to the upper surface of the base 10 to facilitate the movement of patients in wheel chairs or walking onto the base for examination, especially for vertical table work, and to permit positioning of the panel 20 in an out of the way location.

The right hand end member 20 is made of a polyester glass material with a foam core.

A first vertical mast 24, and a second vertical mast 26, are coupled to the base 10. Each mast defines a center line axis extending generally in a vertical direction.

Each of the masts 24, 26 comprises a portion of aluminum tubing having a generally polygonal cross-section.

Figure 10B:
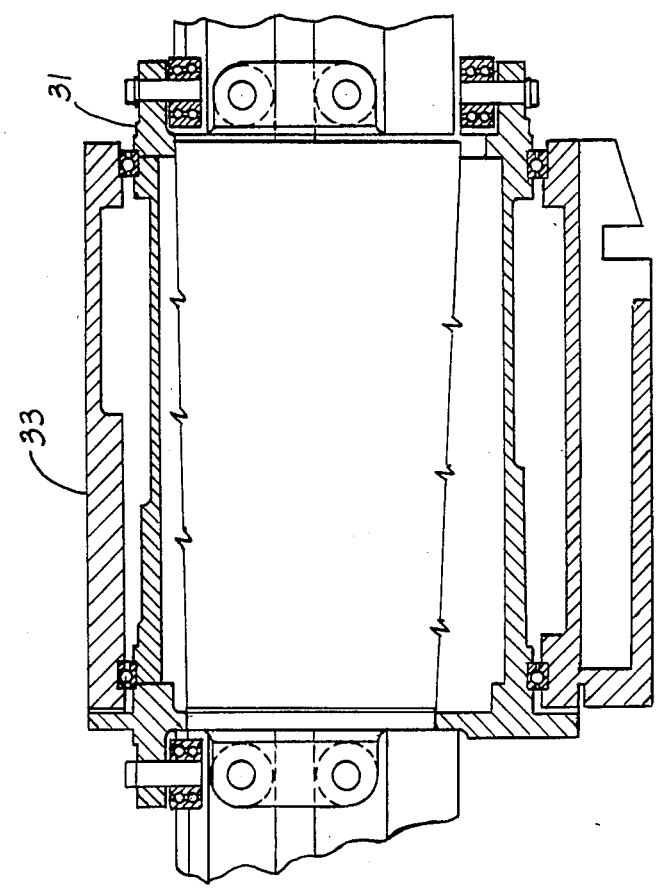
FIGS. 10 and 10A are detail drawings illustrating a portion of the system illustrated in FIGS. 1 and 2, and FIGS. 11–13 are illustrations showing simplified additional embodiments of the present invention.
Figure 10A:
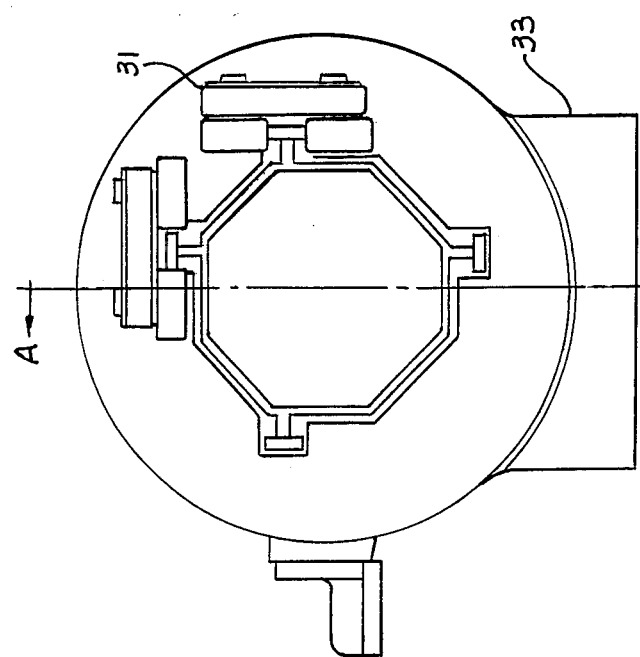

An x-ray tube head 28 of known type is coupled to the first mast 24 by articulated coupling structure. The coupling structure includes a vertical carriage assembly 30 including a vertical carriage member 31 (see FIGS. 10A and 10B) which is mounted for vertical movement up and down the first mast 24 and which forms a vertical carriage to which the remainder of an articulated x-ray tube head support structure is attached.

The vertical carriage assembly also comprises a collar member 33 which rotates clockwise and counterclockwise about the axis of the mast 24. Vertical movement of the carriage assembly is controlled by a brake and is restricted by vertical carriage stops at the top and bottom of the mast 24. Appropriate spring counterbalancing is applied to exert an upward force on the vertical carriage member which is approximately equal to the weight of the vertical carriage assembly, plus its payload. These braking and counterbalancing elements are of known variety and can easily be supplied by those of ordinary skill in the art.

The vertical carriage member 31 surrounds the mast and has rollers that engage and ride on the mast 24. The collar member 33 rotates about the vertical carriage member 31 to provide rotation about the first mast center line axis.

Extending outwardly from the collar member 33 is a first arm 32, which rotates and moves vertically in unison with the collar member 33.

A second arm 36 is mounted to the first arm 32 for pivotal motion about a vertical axis extending through a pivot point 34, displaced from the first mast center line axis.

The second arm 36 defines a longitudinal axis designated by reference character 42.

Figure 3:
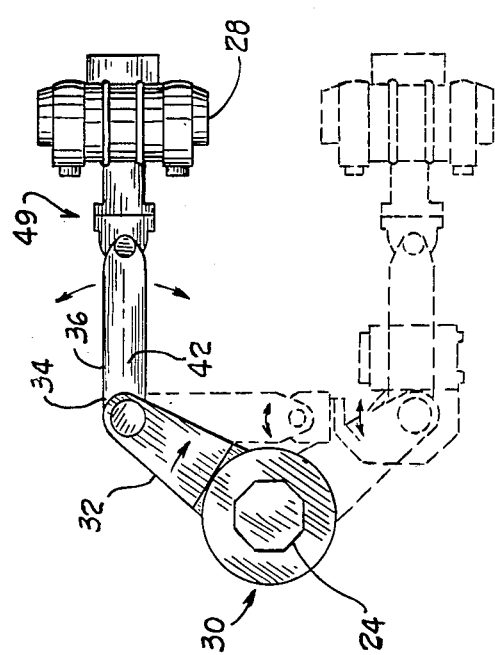
FIG. 3 is a detailed plan view illustrating a portion of the system of FIGS. 1 and 2.

FIG. 3 shows a plan view of the articulated arm structure described above for supporting the tube head 28 to the mast 24.

Figure 4:
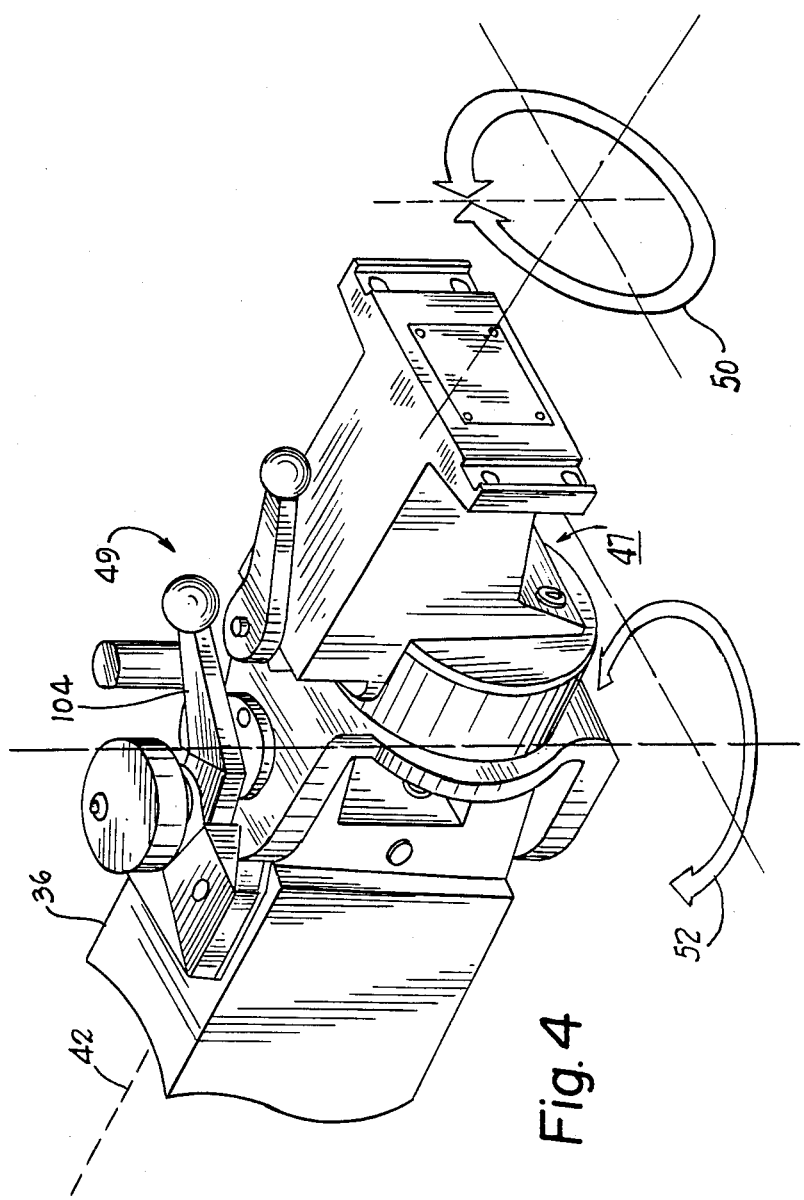
FIG. 4 is an isometric drawing illustrating in detail another portion of the system illustrated in FIGS. 1 and 2.

The x-ray tube head 28 is mounted on the outer end of the second arm 36. The x-ray tube head 28 comprises a known type of x-ray tube assembly 44, and a known type of collimator 46. The x-ray tube head is mounted for a variety of rotational motion about the end of the second arm 36, by apparatus as shown in FIG. 4.

Pivoting apparatus 49 supports the tube head for rotation about a vertical axis generally perpendicular to the second arm axis 42. This motion is described by the circular arrows 52. See also FIG. 3. Apparatus 47 is provided for mounting the tube head for rotation movement about horizontal axis intersecting the vertical axis perpendicular to the axis 42 and defined by the arrows 52. This rotational motion is described by the circular arrows 50. Detent apparatus can be provided in the pivot apparatus 47 and 49 to enable easy operator location of the "zero" angle positions for the tube head at which the tube is positioned to propagate radiation vertically down, and is aligned orthoganal to the second arm 36. Thirdly, the x-ray tube itself is supported on trunnions for tilting rotation about a horizontal axis perpendicular to the second arm axis 42.

It can be seen from the foregoing description of the articulated mounting of the tube on the first mast 24 that enormous flexibility is afforded regarding the location and orientation of the x-ray source 28. In fact, the x-ray source 28 can be positioned at virtually any location above or below the table, within the limits of the length of the mast 24 and of the arms. Within the limits of the system geometry, the tube can be tilted in virtually any direction with respect to the orientation of the table top 12. It can also be seen that the x-ray tube can be moved from a location under the table top 12a to a location over the table top 12a without the need for moving the table top 12a at all, and consequently without the need for disturbing a patient lying on the table.

A spot film device and/or a filmer assembly, generally designated at reference character 60, is movably coupled to the second mast 26. A portion of the coupling mechanism comprises a vertical carriage assembly 62. The vertical carriage assembly 62 comprises a vertical carriage member which moves up and down on the mast 26, and a collar member attached to the carriage member which rotates with respect to the carriage member and the mast. The construction of the vertical carriage assembly 62 is analogous to that described above in connection with the vertical carriage assembly 30. Rotation of its collar member is described by the arrows 64.

The spot film device and/or filmer assembly 60 is thus movable vertically with respect to the mast 26, and can orbit about the center line axis defined by the mast 26. In this way, when the spot film device 60 is not being used, it can be manually orbited away from the general vicinity of the x-ray table, to avoid interference with radiographic work. The spot film device is also spring counterbalanced to facilitate manual vertical adjustment.

Additionally, pivot apparatus is coupled between the spot filmer device and the collar member to provide manual rotation of the spot film device pivoting about a horizontal axis substantially intersecting the axis of the second mast 26, this horizontal axis also being defined by the vertical location of the carriage assembly 62. This permits rotation of the spot filmer for vertical table fluoroscopic work and for rotation to alternate park (storage) positions to the side, above or to the rear of the table. In the rear park position vertical patient access is non-obstructed by the filmer which is a distinct clinical advantage.

A spring counterbalance mechanism within this pivot allows rotation of the filmer about the mast with ease even though its center of gravity is substantially offset from the axis. This mechanism allows motion in both directions about the axis.

Reference to the exploded view of FIG. 2 illustrates in more detail the manner of coupling of the spot film device and fluoro imaging device to the collar member. This coupling is accomplished by way of a bracket 66 which defines a generally forked configuration into which the spot film device can be mounted in known fashion.

FIG. 2 (Section A—A) also illustrates in cross setion track structure for coupling the masts 24, 26 to the base 10. A track set 68 having I-shaped track structure 68 is defined by the base member 10, and extends along a straight line generally parallel to the longitudinal dimension defined by the x-ray table top member. A first carriage 70 is slidably engageable in the inner portion of the I-shaped track element 68a and to a C-shaped member 68b to afford low friction movement along the direction of the track. The carriage member 70 defines a recessed portion 72 into which the lower end of the mast 24 can be manually inserted. Appropriate hand actuable snap locks are provided to hold the mast in the recess 72. When the carriage member 70 is engaged in the track 68, and the mast 24 inserted in the receptacle portion 72, the entire mast 24, and all its payload, are manually and easily movable along the direction of the track 68.

A carriage member 74 is provided for similarly carrying the mast 26. The carriage member 74 is slidably engageable in the outer portion of the I-shaped track member 68a and in the C-shaped member 68b. The carriage member 74 defines a recessed portion 76 into which the lower end of the mast 26 can be inserted. Thus inserted, and with its carriage member mounted in the track 68, the second mast and its payload is also movable manually along the path defined by the track 68.

FIG. 2 illustrates, for purposes of completeness, a high voltage tank 81 and control console 82 for providing the electrical power for operating the spot film device, the tube head, and all electromechanical system components, in accordance with predetermined procedures. The high voltage tank 81 and control console 82 are of known type and can be provided by one of ordinary skill. The high voltage tank and control console are coupled to the tube head and spot film device and other components by appropriate cabling, which is not illustrated in an effort to avoid obfuscating the mechanical aspects of the present invention.

The respective movements of the masts 24, 26 can be independent of one another. In some operating modes, however, it is desirable for the masts 24, 26 to execute ganged movement, i.e., movement in unison. For this purpose, linking structure 80 (see FIG. 5A) is provided for decouplably linking together the carriages 70, 74, so that they and the masts 24, 26, move in unison, or separated, as desired.

The coupling structure comprises a solenoid actuated movable hook 80a on one carriage member, which is releasably engageable with a pin 80b on the other carriage member. The hook can be manually disengaged. The coupling is used when in fluoro mode, table horizontal, with variable S.I.D., and, in the table vertical fluoro mode, with fixed S.I.D.

Figures 5, 5A:
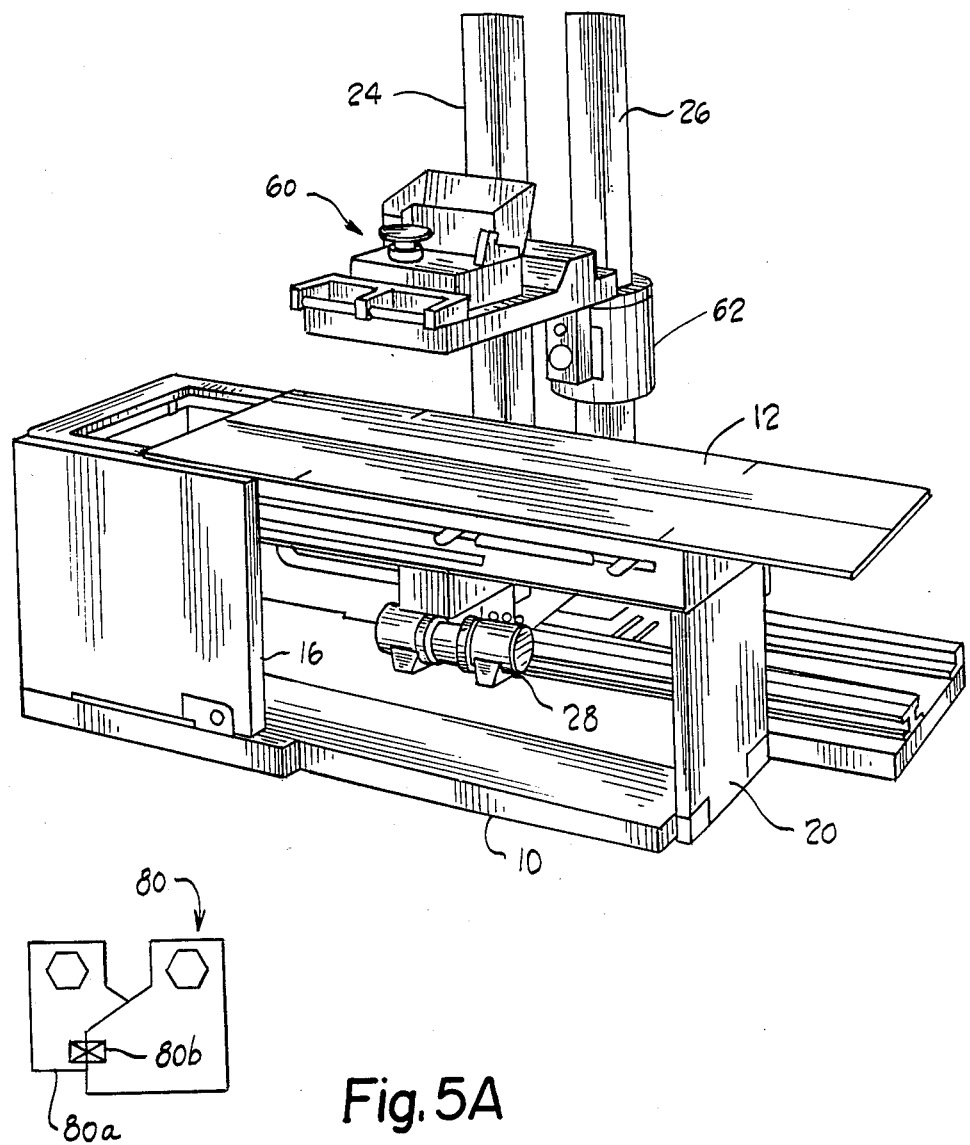
FIG. 5 is an isometric view depicting the system of FIGS. 1 and 2 deployed in a horizontal table fluoroscopic mode configuration.
FIG. 5A is a plan view illustrating details of a portion of system illustrated in FIGS. 5 and 2.

It can be seen from FIGS. 1, 2 and 5 that, although the masts 24, 26 are generally movable independently of one another, the masts cannot obviously be precisely lined up with one another. Rather, there is a certain minimum center to center spacing between the masts.

It will further be seen that, due to the offsetting (displacement) of the x-ray tube head from the mast 24, because of the articulated arms 32, 36 coupling the tube head to the mast, the tube head can be extended to be precisely vertically aligned with the spot film device 60.

This could not be achieved without the offsetting of the tube head from the mast 24.

This offset could optionally be achieved with the tube head being slidable along an arm, rather than by the pivot articulation described here.

When it is desired to execute a horizontal fluoroscopic technique, the tube head is manually moved by way of its articulated coupling structure and vertical carriage member, to a fixed height beneath the table. The tube head is oriented to direct radiation vertically upwardly through the table, and is precisely vertically aligned with the spot filmer 60, attached to the other mast 26, which is in this configuration above the table and above the patient's body. The fluoro device can be moved vertically while the tube remains vertically stationary to vary the S.I.D.

FIG. 5 illustrates the system of this invention operating in the above described vertically aligned horizontal fluoroscopic mode. In this configuration, the masts 24, 26 are linked together for movement in unison, and the tube head 26 is precisely vertically aligned with the spot film device 60. In this configuration, the entire assembly of masts 24, 26, tube head 28, and spot film device 60 can be moved in unison longitudinally over various portions of the patient's body, in an operation known as "panning". Also, the table top 12a can be moved in the directions of the arrows 14 in FIG. 1, to enhance panning.

Preferably, rough positioning for panning is done by moving the masts, and actual panning done by movement of the table top 12a in one or both directions horizontally.

FIG. 5A, mentioned above, illustrates in some detail a plan view of the mechanism for coupling together the carriage members 70, 74, Briefly stated, the mechanism 80 comprises a solenoid actuated movable hook member 80a, attached to one of the carriage members 70, 74, and a pin member 80b attached to the other carriage member. The hook and pin are aligned such that, when the carriage members 70, 74 are moved together, the hook will ride over and engage the pin, thus holding together the carriage members 70, 74 for movement in unison. When it is desired to decouple the carriage members, the solenoid is actuated to cause the hook to retract and disengage from the pin, upon which the carriage members 70, 74 can be manually separated. Alternately, the hook member can be moved to disengage from the pin by the manual application of force.

The table assembly, as noted above, is tiltable about a horizontal pivot axis near its center, relative to its length, the pivot axis being perpendicular to the longitudinal direction defined by the table top. FIG. 1 shows the table top tilted to a vertical position as indicated by the phantom at reference character 88. FIG. 2 illustrates the track structure 90 associated with the side panel members 16, 18, into which the support tilt frame 12c is mounted, in association with roller bearing structure, for longitudinal sliding movement.

FIG. 6 illustrates the sliding and pivoting capabilities of the table top 12a in more detail. The support tilt frame member 12c is mounted for translation and rotation relative to the side panels 16, 18, about a pivot axis 96. Roller bearing structure, such as at 98, mounts the support tilt frame for sliding motion with respect to the side panels 16, 18. In use, when it is desired to tilt the table from a horizontal to a vertical configuration, the table is first slid to the left as shown in FIG. 6, (in phantom). The left hand roller bearing is released from the track when a pawl 83 is properly retaining the right roller bearing 96. This automatically latches when the table has been moved sufficiently to the left. A clearance gate 99 allows vertical passage of the support tilt frame 12c past bearing 98. The table is then subsequently rotated in a clockwise direction about the pivot axis 96 until it reaches its vertical orientation, as indicated by the arrow 100. By moving the table to the left prior to tilting it, the table top member 12a remains substantially in a central location with respect to the base 10 even after tilting to the vertical mode. This feature thus reduces the area of the "footprint" of the x-ray system by keeping the table top near the center of the base in all configurations. After the table top has been rotated to its vertical configuration, the right hand end panel 20 can be lowered by pivoting in a clockwise direction as shown in FIG. 1 (in phantom) to form a ramp which can facilitate movement of a patient in a wheel chair or walking onto the base.

It can be seen from the drawing of FIG. 6 that, in order to tilt the table from its horizontal to its vertical position, the table assembly must be moved to the left, as shown in phantom in FIG. 6. When the table assembly is moved to the left, to the point shown in phantom, it is then tilted to the vertical in the direction of the arrow 100 by an operator. It should be noted that, during tilting, the table is effectively supported about its pivot axis, which is located near its central portion of the table relative to its longitudinal dimension, and the table does not slide downwardly during tilting, but rather its motion is solely rotational.

Figure 7:
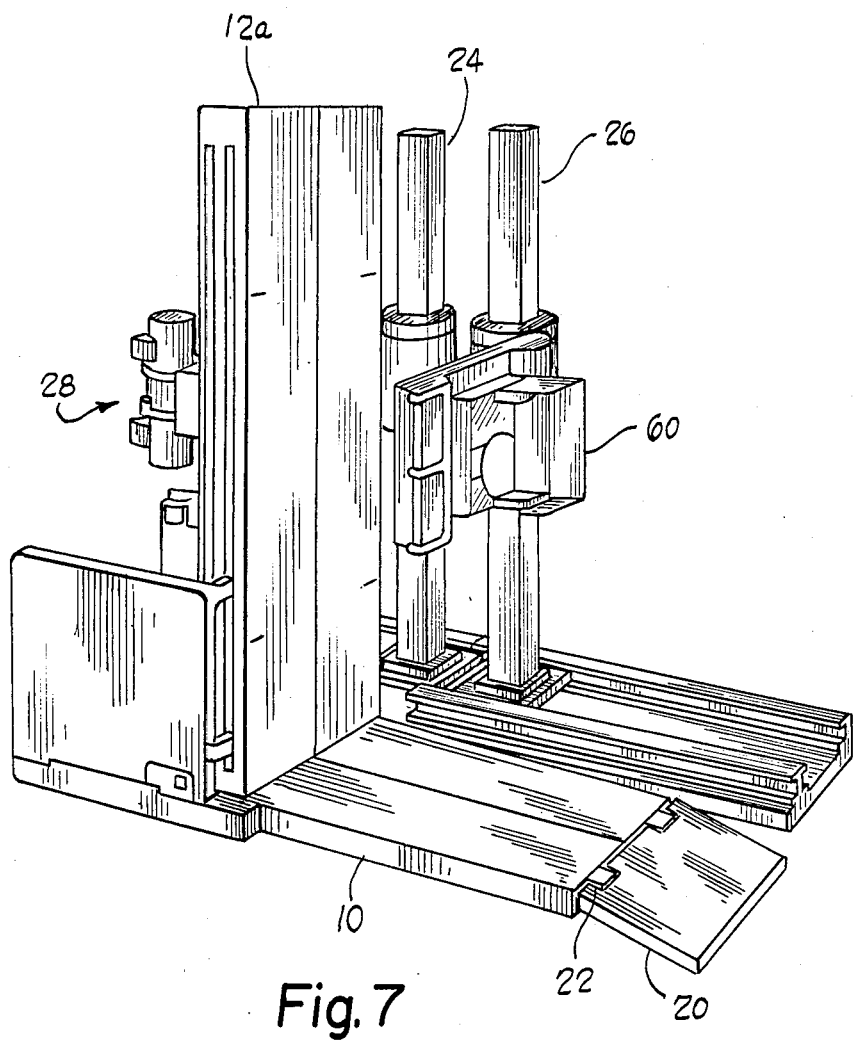
FIG. 7 is an isometric view of a system as shown in FIGS. 1 and 2 deployed in a vertical fluoroscopic configuration.

FIG. 7 illustrates the system of this invention in one of its operating mode with the table top 12 in the vertical position.

The relative movements of the various components of this system, such as of the tube head, spot filmer, masts, and table top, are controlled by means of electrically and/or mechanically operable locks or brakes of known type, in order to stabilize the positioning of the various movable components of the system with respect to one another to maintain a constant relative orientation of these components appropriate for the particular operating mode selected. For example, sliding motion of the masts along the track 68 is inhibited by solenoid actuable brakes which are in turn actuated by a foot pedal, or by control panel buttons, and which have manual override capability. X-ray table top positioning is also controlled by electric brakes. Motions of the tube head with respect to the mast 24 are controlled by manually operable locks or brakes of known type. Vertical and orbital motion of the tube head and spot filmer about their respective masts are controlled by manually operable locks.

The mast 26, being movable with respect to the mast 24, can be manually moved, or parked, near the right hand end of the track 68 as shown in FIG. 1. This flexibility assists in getting the spot filmer and its associated mast out of the way to avoid interference when radiographic imaging is being executed. Alternately, the mast 26, and all the components carried on it, as well as the carriage member 74, can be removed manually from the system altogether. This is done by removing the mast 26 from the receptacle portion 76, and then by sliding the carriage member 74 off the end of the track 68. Such a configuration is beneficial when the system is to be used as a "radiographic only" system, and fluoroscopic imaging is not desired. This feature also implies that the system S can be provided for radiographic use only by the omission altogether of the mast 26, spot filmer 60, carriage member 74 and the associated components. Where it is desired to practice only radiographic techniques, all these elements can be eliminated entirely. This convertability between a radiographic only, or an R/F, system, in conjunction with the basic concept further enhances the uniqueness of this invention. Other known systems are too integrated to form two distinctly different systems without major design changes.

All movable elements are designed or counterbalanced in a manner to permit easy manual movements. No cranks, or mechanisms providing mechanical advantage, or power assists are used in this embodiment. However, these components can be powered or counterweighted using methods known to the state of the art.

An in table cassette cabinet, commonly referred to as a bucky, is incorporated in the table top assembly.

Figure 8:
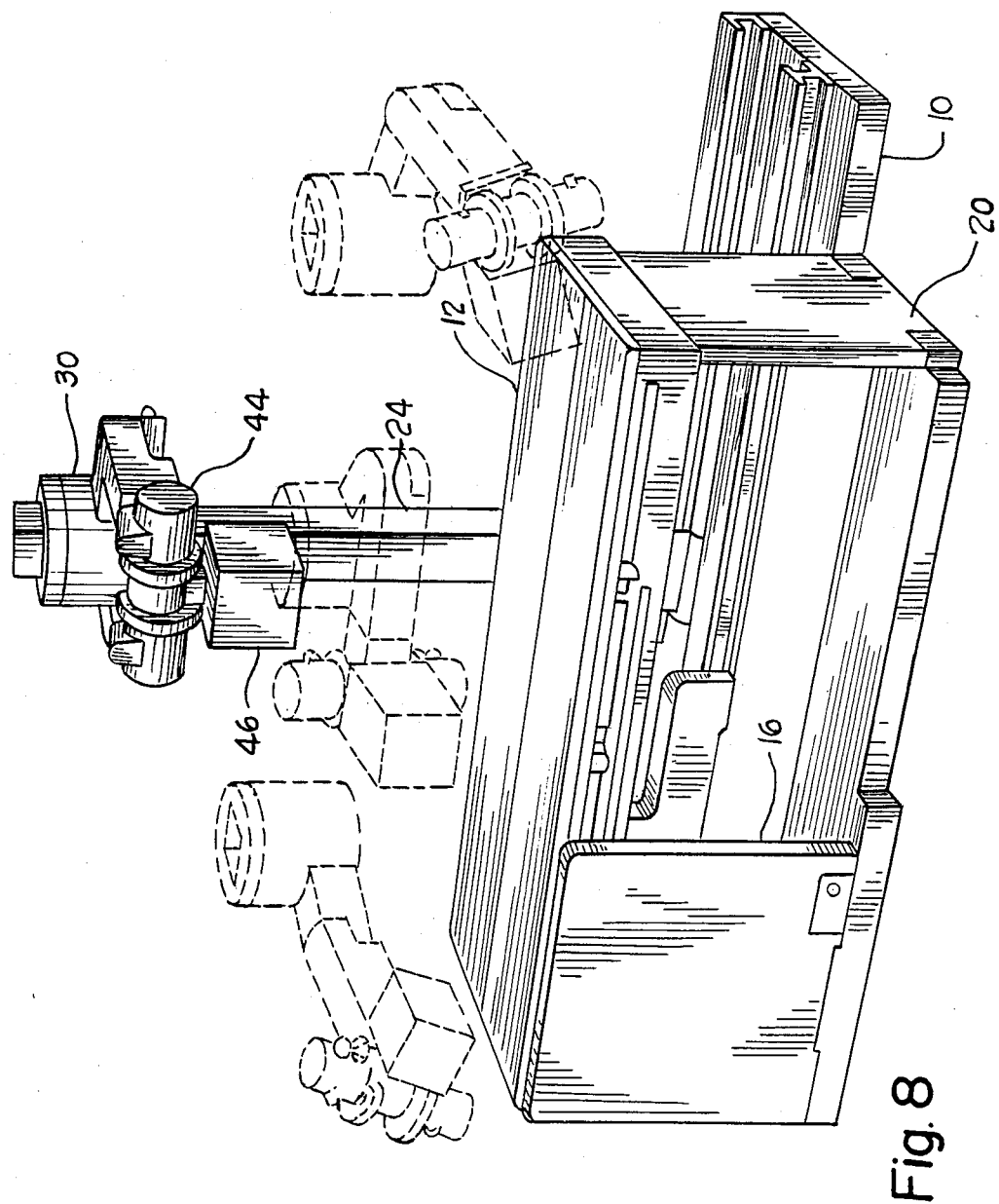
FIG. 8 is an isometric view of a system as shown in FIGS. 1 and 2 adapted for use in a radiographic only operating mode.

FIG. 8 illustrates the system of this invention operating in its so-called "radiographic only" configuration. Note that in this configuration the advantages of the offset x-ray tube support arm and central pivoting table concept continue to result in the advantages of a short length system with enormous patient coverage and procedure capability. In this configuration, the product portability is increased and packaging volume and weight is reduced.

This convertibility feature allows the user to deploy an R/F system as radiographic only or with the fluoroscopic feature without resorting to ordering different versions from the manufacturer. This again enhances the utility.

Another unique advantage of this system is the resulting ease of movement of the various components during change from one clinical procedure to another. Due to the fact that the spotfilmer and its associated mast can be parked, it is not necessary for the the user to move the fluoroscopic payload when doing radiographic procedures along with the radiographic payload. For example, if both the radiographic unit and spotfilmer were coupled to a single mast ("C" arm configuration) both units would be moved in all procedures. Furthermore, the tendency for damage is much greater with movement of massive and cumbersome "C" arms in both rotation and translation, especially in tight quarters such as a military isoshelter.

The present system is designed to be manually knocked down and reassembled without the aid of tools. That is to say, wherever fastening and unfastening of components one from another is required, that fastening is provided by the use of hand acutable apparatus, such as snap locks, hand operable screw apparatus, and the like.

The system of this invention is modular in nature, in that it can be broken down into subassemblies which can be stored in resuable containers, each dedicated to a particular subassembly or subassemblies, for transport. Each of the subassemblies is designed to be sufficiently light in weight to be handled efficiently by a team of four men.

As mentioned above, the base member 10 is of a segmented construction, the segments of which are hinged together for folding for easier transport.

The system S is transportable in 13 containers. Each container is dedicated for storage of predetermined system components. Generally speaking, each container comprises the same kinds of material, fasteners, packing material and other components. Aspects of the containers are illustrated in FIGS. 9A-9C. Referring to FIG. 9A, a container 150 includes a top portion 152 and a bottom poriton 154. Each container top portion includes packing material glued therein, and positioned appropriately to maintain stored system components in a desired orientation within the container 150. The packing material is illustrated, for example, in FIGS. 9B and 9C at reference character 156. Each container bottom also includes packing material glued appropriately to its inside surface. The packing material 156 includes polyethylene foam.

Fasteners, such as at 158 in FIG. 9A, are provided to selectively hold together the top and bottom portions of the container 150. Each fastener includes a clamp riveted to the container bottom and a keeper riveted to the container top. A clamp guard riveted to the container bottom protects the clamp when the container is closed.

Handles, such as at 160, 162 are provided at either end of the container 150 to assist in facilitating hand carriage of the container. Each handle is held in position by a bracket which is riveted to the container.

A gasket 166 is located in the edge frame of the container top. When the container is closed, the gasket forms a water-tight seal.

A pressure relief valve 168 is provided in each container, which automatically opens to equalize the pressure inside the container with ambient pressure.

Certain simplified embodiments of a system such as described above also yield important advantages without resort to the complexity of the system described in FIGS. 1-4. Such a system is illustrated in FIG. 11.

Figure 11:
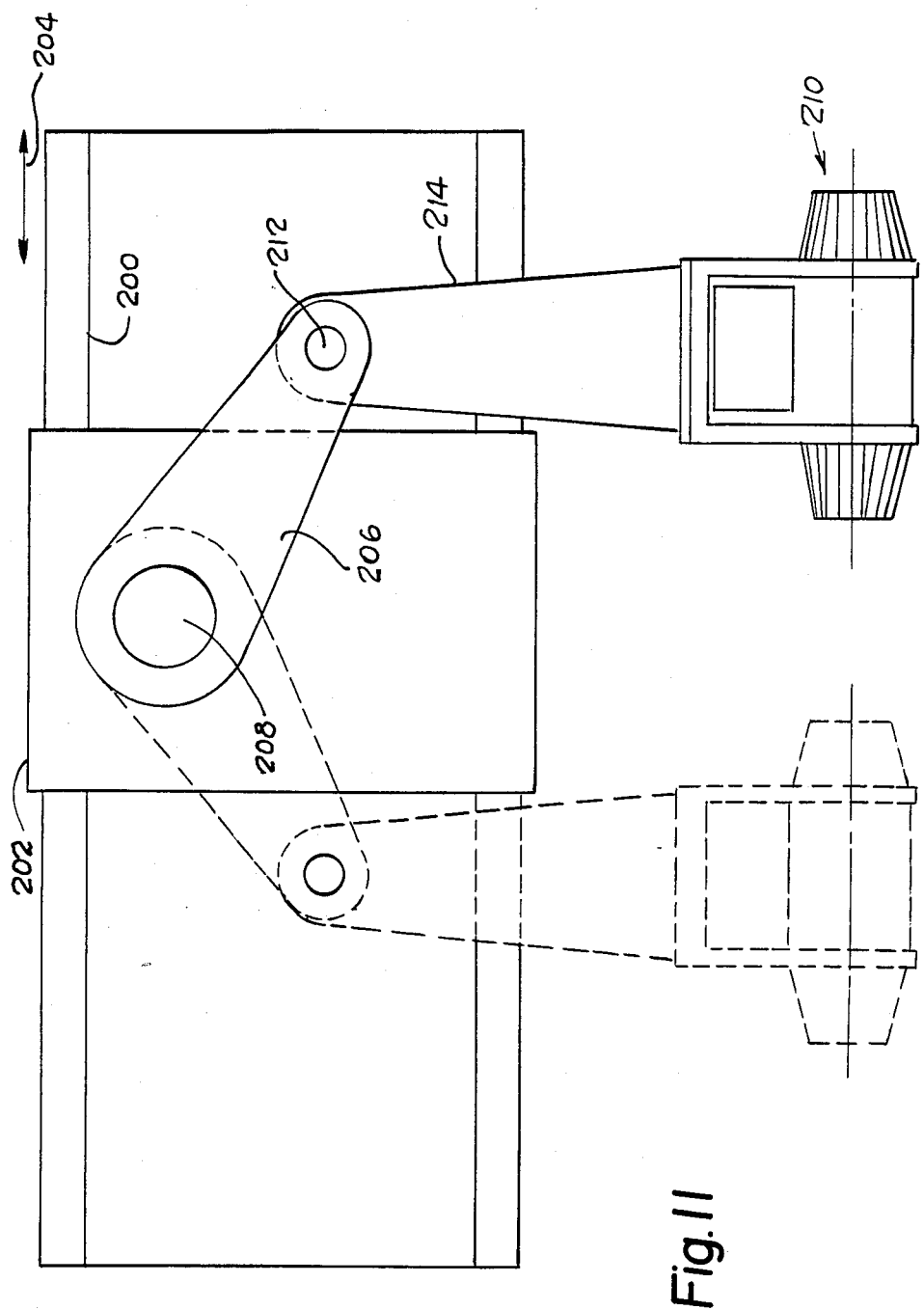

FIG. 11 illustrates a track structure 200 upon which rides a carriage member 202 which is movable in a direction given by the arrows 204. An arm 206 is pivotally mounted to the carriage for rotation about an axis described by a pivot point 208. An x-ray source 210 is mounted for rotational movement with respect to an axis 212 parallel to the pivot axis 208 and extending through the arm 206. In the instance of FIG. 11, the x-ray source 210 is coupled for rotational movement about the pivot 212 by an arm 214. It is to be understood, however, that the x-ray source 210 could be positioned such that a pivot axis 212 passes through the source, i.e., the x-ray source could be directly pivotally mounted to the arm 206.

A very decided advantage results from this structure. The x-ray source 210 is offset from the pivot axis 208 by a distance equal to the distance between the pivot axes 208, 212. This means that the total possible excursion of x-ray tube motion in a direction parallel to the arrows 204 is considerably longer than the length of the track structure 200. This feature thus enables x-ray source coverage over a distance substantially longer than the track structure to which it is ultimately mounted This double pivot arrangement thus enables the use of relatively short tracks, which occupy relatively little area, while still retaining flexibility of motion of the system.

Figure 12:
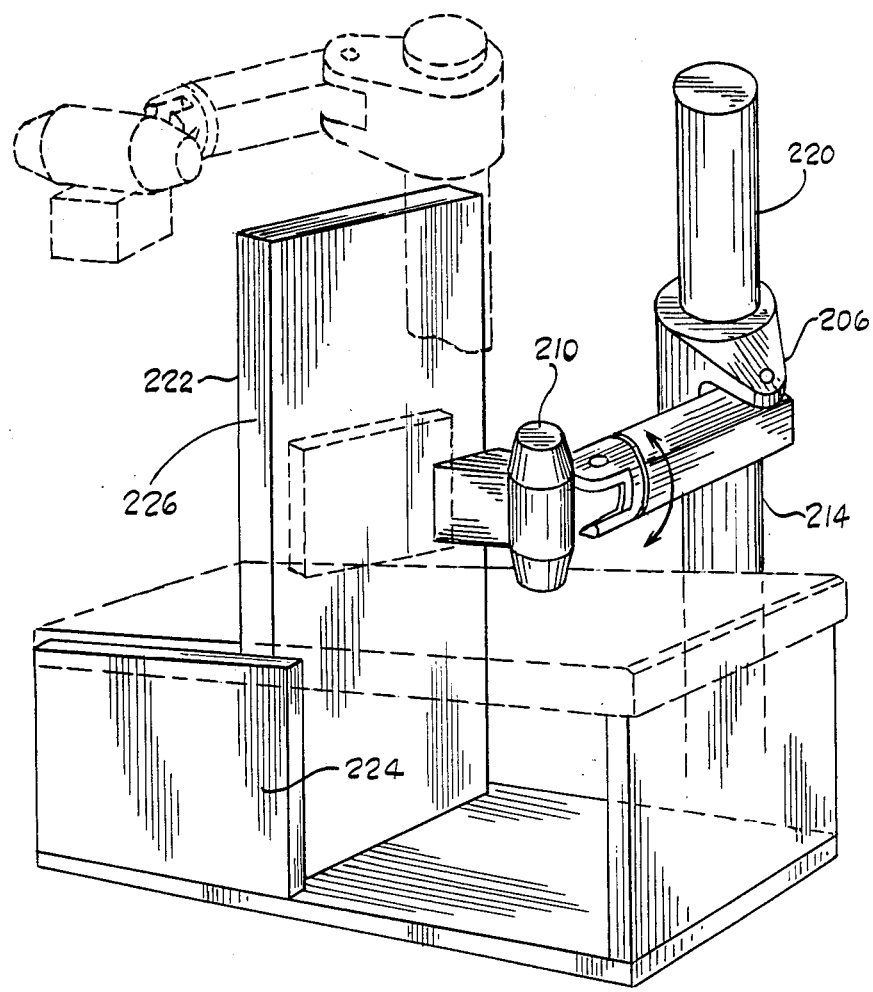

FIG. 12 illustrates an embodiment corresponding to that of FIG. 11, but with some additional elements. In FIG. 12, the arms 206, 214 are mounted for rotation on a mast 220 which in turn is mounted for longitudinal motion on a track similar to that described in connection with FIGS. 1 and 2. The x-ray source 210 is mounted for pivotal motion about an axis which is substantially coincident with the axis of the second arm 214. A patient support means, in this case an elongated table 222, is also provided. The table 222 is supported for pivotal movement between horizonal and vertical positions, about a pivot axis 224, which is generally centrally located with respect to the longitudinal dimension defined by the table's shape, the pivot axis being horizontal.

Thus, the embodiment of FIG. 12 adds to the embodiment of FIG. 11 the additional features of pivoting the tube about the axis of the second arm, and pivoting the patient support table about an axis near its center with respect to its longitudinal dimension. The provision of the tiltable table with the pivot apparatus centrally located, combined with the two-pivot apparatus of FIG. 11, results in a system which further minimizes the length of the overall area "footprint" required to achieve x-ray tube movement with respect to the patient for varying S.I.D.

Optionally, an in-table cassette carriage, or "bucky" 226 can be added to the table 222.

Tilting the table in its central region, rather than at one end or another, as done in the prior art, combines with the other features of the FIG. 11 embodiment to further minimize the amount of longitudinal length required to operate the system in many different modes. As shown in FIG. 12, the tube can project a horizontal beam from either side of the vertically positioned table, and from a variety of distances in each direction. The system of FIG. 12 is also capable of doing lateral work, wherein the x-ray beam is projected horizontally, transverse to the table top.

In accordance with a further embodiment, the embodiment of FIG. 12 can be enhanced by the addition of pivot means, such as described in connection with FIG. 4, for mounting the x-ray tube for pivotal motion about a pair of orthogonal axes at least one being orthogonal to the axis defined by the second arm. This added mechanism results in a radiographic system capable of a wide range of x-ray source positioning and beam angles, including for oblique work. Counting the tiltable patient support means, the apparatus of FIG. 12, thus enhanced, provides no less than six different types of rotational tube/patient relative motion, as well as linear motion made possible by the track mounted mast.

Figure 13:
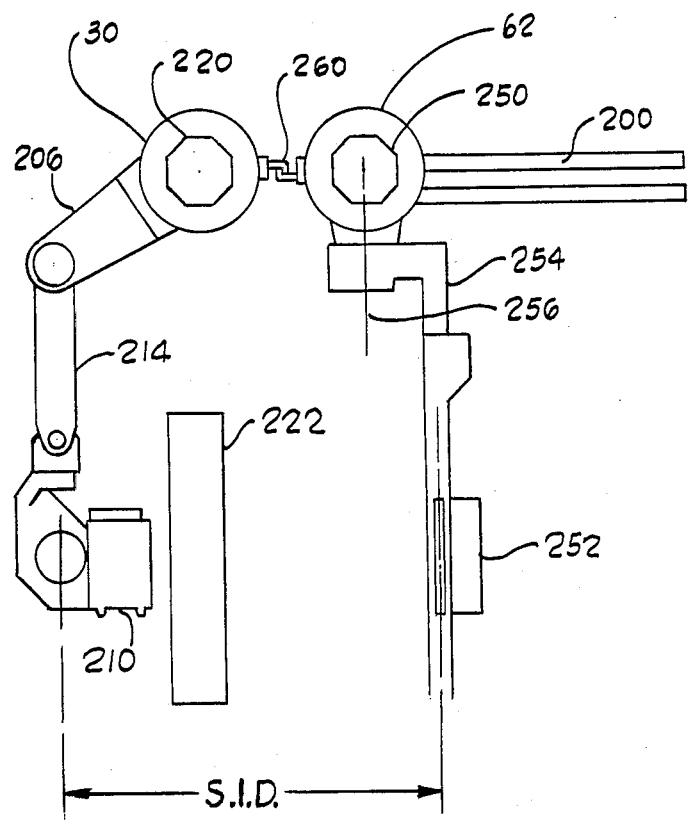

Flexibility of the system of FIGS. 11 and 12 is further enhanced by adding apparatus as shown in FIG. 13. FIG. 13 illustrates the addition to the system of a separate mast 250, and a filmer device 252 coupled to the mast 250 by way of a rotatable arm structure 254. Alternately, the arm 254 can carry a fluoroscopic device.

As described in connection with previous embodiments, the mast 250 is movable longitudinally along the guide structure which defines a path parallel to the longitudinal dimension of the table top.

An important aspect of this embodiment is that the arm structure 254 can offset the fluoro device or filmer device with respect to the masts. In the plan view of FIG. 13, the arm 254 is rotatable about a horizontal axis 256 which intersects the axis of the mast 250. The arm structure 254 can be rotated about the axis 256 to place the fluoro device carried on the arm 254 more distant from the table top than the mast 250. Thus, the offsetting of the fluoro device from the mast 250 enables a greater S.I.D. than would be possible if the fluoro device were simply coplanar with the axis 256. Thus, in a sense, the offsetting of the fluoro device in effect "extends" the track upon which the mast 250 rides. The fluoro device can be cantilevered out beyond the extent of the track on which the motion of the mast 250 is limited.

Additionally, the entire arm structure 254 is mounted for orbital rotation about the centerline axis of the mast 250.

Great flexibility and compact system size are achieved with the combination of fluoro device/spot film offset and x-ray source offset. For example, when a great distance is needed between the source and the fluoro device, the masts can be moved to opposite ends of the track, and even more separation can be achieved by positioning the source and the spot film device extending in opposite directions in their offset placement mode. For example, if the track is 6 ft. long, and each offset capability is 2 ft., a spread of 10 ft. can be achieved with a track of only 6 ft.

Of course, where the system of FIG. 13 is operated in a vertical fluoroscopic mode, the masts can be coupled together at their minimum spacing for movement in unison, and the offset feature, as described in detail above, enables the precise vertical alignment of the source with the radiation detector. This alignment is maintained, because of the coupling, during all relative motion between (1) the source and fluoro device and (2) the patient table.

Additionally, means 260 is provided to couple the vertical carriage assembly of the source to the vertical carriage assembly mounted on the fluoro mast. These vertical carriage assemblies correspond to the elements 30, 62, as shown in FIGS. 1 and 2. When this is done, and the system operated in a vertical fluoroscopic mode, the x-ray beam maintains its alignement with the fluoro device during vertical movement of the source and fluoro device. Thus, the source and fluoro device move vertically in unison.

In vertical fluoro operation, the system operates with a fixed S.I.D., whereas in horizontal table fluoroscopy the system operates with a variable S.I.D. In this mode, the x-ay tube is stationary vertically while the filmer or fluoro device can be vertically moved. Vertical alignment, however, is maintained because of the coupling between the masts and the offset structure. The pivot capability about the axis 256 and about the central axis of the mast 250 provides additional degrees of rotation of the filmer to allow unique park positions wherein the filmer can be swung out of the way to any of a plurality of park positions, such as the the rear of the table. In many prior art systems, the filmer remains somewhat over the table when in the park position, and encumbers radiographic procedures.

The versatility of the present system is expressed in concrete terms by the following list of the types of radiographic and fluoroscopic studies which can be performed with the present system, which is lightweight, as well as relatively compact, and without the aid of any other equipement:

RADIOGRAPHIC/FLUOROSCOPIC PROCEDURES

1. Fracture of vault of skull (consciousness)
2. Fracture of face bones
3. Fracture and fracture dislocation of spine w/o cord lesion
4. Fracture of ribs
5. Fracture of pelvis
6. Fracture of clavicle
7. Fracture of scapula
8. Fracture of humerus
9. Fracture of radius-ulna
10. Fracture of handbones 11. Fracture of femur
12. Fracture of tibia-fibula
13. Fracture of tarsal-metatarsal
14. Dislocation of shoulder
15. Dislocation of elbow
16. Dislocation of wrist
17. Dislocation of hip
18. Dislocation of knee
19. Dislocation of ankle
20. Disloation of cervical spine
21. Dislocation of spine, complications
22. Brain laceration and contusion w/wound
23. Intracranial hemorrhage w/o pen. or perf. wound
24. Intracranial hemorrhage w/wound
25. Traumatic pneumo and hemo chest thorax w/o pen. or perf. wound
26. Traumatic pneumo and hemo thorax w/wound
27. Lung injury w/o open wound
28. Lung injury w/open wound
29. Gastrointestinal tract w/open wound
30. Liver injury w/open wound
31. Liver injury w/o open wound
32. Spleen injury w/open wound
33. Spleen injury w/o open wound
34. Pelvic organ injury w/open wound
35. Open wound back w/o complications
36. Open wound, head, neck and trunk w/o complications
37. Traumatic amputation arm and hand w/o complications
38. Open wound, hip, and thigh complications
39. Open wound, knee, lower leg, and ankle w/o complications
40. Open wound, foot w/o complications
41. Traumatic amputation foot w/o complications
42. Traumatic amputation leg w/o complications
43. Multiple open wounds, upper extremities w/o complications
44. Multiple open wounds, lower extremities w/o complications
45. Burn, face, head, and neck 2 w/o complications
46. Burn, face, head, an neck 3 w/o complications
47. Burn, trunk 2 w/o complications
48. Burn, trunk 3 w/o complications
49. Nerve injury-spinal cord, cervical w/open wound
50. Nerve injury-Thoracic and Lumbar spine cord w/open wound
51. Nerve injury-sacral spinal cord w/open wound
52. Pulmonary tuberculosis
53. Meningococcal infection (includes meningococcal meningitis)
54. Gas gangrene (various extremities)
55. Aseptic meningitis/encephalitis
56. Malignant and benign neoplasms (affected past)
57. Diseases of the ear and mastoid process
58. Diseases of veins and lymphatics and other vascular diseases
59. Hernia
60. Other diseases of intestine and peritoneur It is to be understood that the foregoing detailed description is intended as illustrative rather than exhaustive, of the invention. It is to be recognized that those ordinary skill may be able to make certain additions to, deletions from or modifications to the embodiment described above without departing from the spirit or the scope of the invention as expressed in the appended claims.

We claim:

1. A diagnostic x-ray imaging system comprising:
   (a) base;
   (b) an x-ray table assembly defining a longitudinal dimension;
   (c) means for supporting said x-ray table assembly above said base;
   (d) a first vertical mast defining a first vertical mast axis substantially perpendicular to said base;
   (e) a first vertical carriage assembly copled to said first vertical mast for vertical movement up and down said first vertical mast and for rotational motion about said first vertical mast axis;
   (f) articulated arm structure comprising a first arm extending outwardly from said first vertical carriage assembly and a second arm having first and second end portions, said first end portion mounted to said first arm for pivotal movement with respect to said first arm about a substantially vertical first arm axis;
   (g) an x-ray tube head;
   (h) means for mounting said x-ray tube head to said second end portion of said second arm;
   (i) a second vertical mast defining a second vertical mast axis substantially perpendicular to said base;
   (j) a second vertical carriage assembly coupled to said second vertical mast for vertical movement up and down said second vertical mast and for rotational motion about said second vertical mast axis;
   (k) an image receptor means defining a substantially planar image receptor area;
   (l) means for mounting said image receptor means to said second vertical carriage assembly; and
   (m) means for mounting said first and second vertical masts to said base for independent translation along a path substantially parallel to said longitudinal dimension of said table assembly, said first and second masts being separated by a predetermined minimum distance between their respective axes.

2. The diagnostic x-ray imaging system of claim 1, wherein said x-ray tube head mounting means comprises:
   (a) means for rotational movement of said tube head with respect to a second arm axis; and
   (b) means for rotational movement of said tube head with respect to an axis substantially orthogonal to said second arm axis.

3. The diagnositic x-ray imaging system of claim 2, wherein the x-ray tube head coupling means further comprises means for pivotal movement of said tube head about a trunnion axis.

4. The diagnostic x-ray imaging system of claim 1, wherein said image receptor mounting means comprises means for rotational movement about a substantially horizontal axis orthogonal to said second vertical mast axis for positioning said image receptor means to a horizontal and vertical disposition.

5. The diagnostic x-ray imaging system of claim 4 wherein said image receptor mounting means further comprises means to offset said image receptor means for said second mast axis when said image receptor means is in a vertical disposition.

6. The diagnostic x-ray imaging system of claim 1, further comprising means for decouplably connecting said first and second vertical masts for translation in unison.

7. The diagnostic x-ray imaging system of claim 1, wherein said first vertical carriage assembly comprises a vertical carriage member mounted for vertical movement up and down said first vertical mast, and a collar member mounted to said vertical carriage member for rotational motion with respect thereto.

8. The diagnostic x-ray imaging system of claim 1, wherein said second vertical carriage assembly comprises a vertical carriage member mounted for vertical movement up and down said second vertical mast, and a collar member mounted to said vertical carriage member for rotational motion with respect thereto.

9. The diagnostic x-ray imaging system of claim 1 wherein the x-ray table assembly comprises:
   (a) a support tilt frame;
   (b) a subframe movably mounted to the support tilt frame for transverse motion with respect to said support frame orthogonal to said longitudinal dimension of the table assembly; and
   (c) a table top member movably mounted to said subframe for longitudinal motion with respect to said subframe parallel to said longitudinal dimension of the table assembly.

10. The diagnostic x-ray imaging system of claim 1, wherein said means for supporting said table assembly above said base comprises pivot means for tilting motion of said table assembly about a substantially horizontal table axis perpendicular to said longitudinal dimension of said table assembly to a horizontal and a vertical disposition of said table assembly and for maintaining said table assembly in a generally central location with respect to the base when the table assembly is tilted to its vertical disposition.

11. The diagnostic x-ray imaging system of claim 1, wherein said means for supporting said table assembly above said base comprises a foot support portion hingedly fastened to said base and decouplable from said table top to tilt to form a ramp leading onto said base.

12. The diagnostic x-ray imaging system of claim 9, further comprising:
   means coupled to said table assembly comprising a cassette holding arrangement for accommodating a cassette containing radiographic film and holding the cassette in a disposition substantially parallel to and below said table top.

13. The system of claim 4 wherein the outward extension of said first arm from said first vertical carriage assembly is sufficiently long to permit vertical alignment of said x-ray tube head and said image receptor means.

14. The diagnostic x-ray imaging system of claim 1, wherein:
   said base comprises a generally flat structure comprising segments hinged together.

15. The diagnostic x-ray imaging system of claim 11, wherein:
   said base comprises a honeycomb aluminum construction.

16. The system of claim 11, wherein:
   said foot support portion comprises a portion of polyester glass with a foam core.

17. The diagnostic x-ray imaging system of claim 1 wherein said table assembly comprises a table top comprised of graphite epoxy composite material.

18. The diagnostic x-ray imaging system of claim 1, wherein said means for mounting said second vertical mast to said base includes means for manual demounting of said second mast from said base.

19. The diagnostic x-ray imaging sytem of claim 1 further comprising:
hand actuatable fastening and assembly means facilitating knockdown reassembly of said system components independently of the use of tools.

20. An x-ray imaging system comprising:
   (a) base;
   (b) an x-ray table top defining a longitudinal dimension;
   (c) means for supporting said table top above said base comprising pivot means coupling said table top to said base for tilting motion of said table top about a substantially horizontal axis perpendicular to said longitudinal dimension of said table top between a horizontal and a vertical dispostion of said table top and for maintaining the table assembly in a generally central location with respect to said base when the table assembly is tilted to its vertical disposition;
   (d) a first vertical mast defining a first vertical mast axis substantially perpendicular to said base;
   (e) a first vertical carriage assembly coupled to said first vertical mast for vertical movement up and down said first vertical mast and for rotational motion about said first vertical mast axis;
   (f) an x-ray source for generating x-radiation along a beam path;
   (g) means for coupling said x-ray source to said first vertical carriage assembly, said coupling means affording sufficient freedom of movement of said x-ray source from a location under said table top, when said top is horizontal, to a position over said table top without moving said table top, and comprising articulated arm structure comprising a first arm extending outwardly from said first vertical carriage assembly and a second arm having first and second end portions, said first end portion mounted to said first arm for pivotal movement with respect to said first arm about a substantially vertical first arm axis;
   (h) a second vertical mast defining a second vertical mast axis substantially perpendicular to said base;
   (i) a second vertical carriage assembly coupled to said second vertical mast for vertical movment up and down said second vertical mast and for rotational motion about said second mast axis;
   (j) an image receptor means;
   (k) means for mounting said image receptor means to said second vertical carriage assembly for positioning said image receptor over said table top when said table top is horizontal; and
   (l) means for mounting said first and second vertical masts to said base for independent translation along a path substantially parallel to said longitudinal dimension of said table top, said first and second masts being separated by a predetermined minimum distance between their respective axes.

21. The diagnostic x-ray imaging system of claim 20 wherein said means for coupling said x-ray source to said first vertical carriage assembly further comprises:
   (a) means for rotational movement of the tube head with respect to a second arm axis, and
   (b) means for rotational movement of said tube head with respect to an axis substantially orthogonal to said second arm axis.

22. An x-ray imaging system comprising:
   (a) a non-tilting base;
   (b) an x-ray table top defining a longitudinal dimension;

(c) means for supporting said table top above said non-tilting base in a substantially horizontal disposition;

(d) a first vertical mast defining a first vertical mast axis substantially perpendicular to said non-tilting base;

(e) a second vertical mast defining a second vertical mast axis substantially perpendicular to said non-tilting base;

(f) means for mounting said first and second vertical masts to said non-tilting base for independent translation along a path substantially parallel to said longitudinal dimension of said table top, said first and second masts being separated by a predetermined minimum distance between their respective axes;

(g) an image receptor means;

(h) means for mounting said image receptor means to said second vertical mast for positioning said image receptor above the table top and along the longitudinal dimension of the table top;

(i) an x-ray source for propagating a beam of radiation along a beam axis;

(j) means for mounting the x-ray source to the first vertical mast for positioning the x-ray source beneath the table top to direct the beam of radiation up through the table top, and for aligning the x-ray source with said image receptor along the beam axis.

23. The x-ray imaging system of claim 22 wherein said means for mounting the x-ray source to the first vertical mast comprises:

(a) a first vertical carriage assembly coupled to said first vertical mast for vertical movement up and down said first vertical mast and for rotational motion about said first vertical mast axis;

(b) articulated arm structure comprising a first arm extending outwardly from said first vertical carriage assembly and a second arm having first and second end portions, said first end portion mounted to said first arm for pivotal movement with respect to said first arm about a substantially firt arm axis; and (c) means coupled to said second end portion for rotational movement of said x-ray source about a second arm axis.

24. The x-ray imaging system of claim 23 wherein said means for mounting the x-ray source to the first vertical mast further comprises means coupled to said second end portion for rotational movement of said tube head with respect to an axis substantially orthogonal to said second arm axis.

25. The x-ray imaging system of claim 23 wherein said means for mounting the x-ray source to the first vertical mast further comprises means coupled to said second end portion for pivotal movement of said x-ray source about a trunnion axis.

26. An x-ray imaging system comprising:
(a) a base;
(b) an x-ray table assembly defining a longitudinal dimension;
(c) means for supporting said x-ray table assembly above said base;
(d) a first vertical mast defining a first vertical mast axis substantially perpendicular to said base;
(e) means for mounting said first vertical mast to said base for translation along a path extending the width of said base and substantially parallel to said longitudinal dimension of said table assembly;

(f) a first vertical carriage assembly coupled to said first vertical mast for vertical movement up and down said first vertical mast and for rotational motion about said first vertical mast axis;

(g) an x-ray tube head;

(h) means for movably coupling said x-ray tube head to said first vertical carriage assembly for positioning said tube head beyond the extent of said first vertical mast mounting means comprising:

(i) a first arm extending outwardly from said first vertical carriage assembly;

(ii) a second arm having first and second end portions, said first end portion mounted to the extending end of said first arm for pivotal movement with respect to said first arm about a substantially vertical first arm axis; and (iii) means coupling said x-ray tube head to said second end portion of the second arm for rotational movement of said tube head about a second arm axis.

27. The x-ray imaging system of claim 26 wherein said means coupling said x-ray tube head to said second end portion of the second arm further comprises means for pivotal movement of said tube head about an axis substantially orthogonal to second arm axis.

28. The x-ray imaging system of claim 26 wherein said means coupling said x-ray tube head to said second end portion of the second arm further comprises mean for pivotal movement of said x-ray source about a trunnion axis.

29. The x-ray imaging system of claim 26 further comprising:

(a) a second vertical mast defining a second vertical mast axis substantially perpendicular to said base;

(b) means for mounting said second vertical mast to said base for translation independent of said first mast along a path extending the width of said base and substantially parallel to said longitudinal dimension of said table assembly, said second mast path being substantially coincident with said first mast path;

(c) a second vertical carriage assembly coupled to said second vertical mast for vertical movement up and down said second vertical mast and for rotational motion about said second vertical mast axis;

(d) an image receptor means defining a substantially planar image receptor area;

(e) means for movably coupling said image receptor to said second vertical carriage assembly for positioning said image receptor beyond the extent to said second vertical mast mounting means comprising:

(i) means for rotational movement about a substantially horizontal axis orthogonal to said second vertical mast axis for positioning said image receptor to a horizontal and vertical disposition; and (ii) means to offset said image receptor means from said second mast axis when said image receptor means is in a vertical disposition.

30. The x-ray imaging system of claim 29 further comprising means for decouplably connecting said x-ray tube head and said image receptor together for vertical movement in unison.

31. The x-ray imaging system of claim 29 further comprising means for decouplably connecting said first and second vertical masts for translation in unison.

32. The x-ray imaging system of claim 26 further comprising means coupled to said x-ray table assembly comprising a cassette holding arrangement for accommodating a cassette containing radiographic film and holding the cassette in a disposition substantially parallel to and below said table assembly.

33. An x-ray imaging system comprising:
(a) a base;
(b) an x-ray table assembly defining a longitudinal dimension and comprising:
  (i) a support tilt frame;
  (ii) a subframe movably mounted to said support tilt frame for transverse motion with respect to said support tilt frame orthogonal to the longitudinal dimension of the table assembly; and
  (iii) a table top member movably mounted to said subframe for longitudinal motion with respect to said subframe parallel to said longitudinal dimension of the table assembly;
(c) means for supporting said x-ray table assembly above said base comprising pivot means for tilting motion of said table assembly about a substantially horizontal table axis orthogonal to said longitudinal dimension of the table assembly to a horizontal and vertical disposition of said table assembly and for maintaining said table assembly in a generally central location with respect to the base when the table assembly is tilted to its vertical disposition;
(d) a first vertical mast defining a first vertical mast axis substantially perpendicular to said base;
(e) a first vertical carriage assembly coupled to said first vertical mast for vertical movement up and down said first vertical mast and for rotational motion about said first vertical mast axis;
(f) articulated arm structure comprising a first arm extending outwardly from said first vertical carriage assembly and a second arm having first and second end portions, said first end portion mounted to said first arm for pivotal movement with respect to said first arm about a substantially vertical first arm axis;
(g) an x-ray tube head;
(h) means for mounting said x-ray tube head to said second end portion of said second arm comprising means for rotational movement of said tube head about a second arm axis;
(i) a second vertical mast defining a second vertical mast axis substantially perpendicular to said base;
(j) a second vertical carriage assembly coupled to said second vertical mast fo vertical movement up and down said second vertical mast and for rotational motion about said second vertical mast axis;
(k) an image receptor means defining a substantially planar image receptor area;
(l) means for mounting said image receptor means to said second vertical carriage assembly comprising:
  (i) means for rotational movement about a substantially horizontal axis orthogonal to said second vertical mast axis for positioning said image receptor to a horzontal and vertical disposition; and
  (ii) means to offset said image receptor means from said second mast axis when said image receptor means is in a vertical disposition; and
(m) means for mounting said first and second vertical masts to said base for independent translation along a path substantially parallel to said longitudinal dimension of said table assembly, said first and second masts being separated by a predetermined minimum distance between their respective axes.

34. The x-ray imaging system of claim 33 further comprising hand actuatable fastening and assembly means facilitating knockdown reassembly of said system components independently of the use of tools.

35. The x-ray imaging system of claim 33 wherein said second arm axis is substantially parallel to said vertical first arm axis.

36. The x-ray imaging system of claim 33 wherein said second arm axis is substantially orthogonal to said vertical first arm axis.

37. The x-ray imaging system of claim 33 further comprising means for decouplably connecting said x-ray tube head and said image receptor together for vertical movement in unison.

38. The x-ray imaging system of claim 33 further comprising means for decouplably connecting said first and second vertical masts for translation in unison.

39. The x-ray imaging system of claim 33, further comprising:
means coupled to said table assembly comprising a cassette holding arrangement for accommodating a cassette containing radiographic film and holding the cassette in a disposition substantially parallel to and below said table top.

40. An x-ray system for examining patients, said system comprising:
(a) a base;
(b) an x-ray table top defining a longitudinal dimension;
(c) means for supporting said x-ray table top above said base for movement with respect to said base;
(d) a first mast;
(e) means for coupling said first mast for translational movement with respect to said base such that said first mast movement is independent from and not in response to said movement of said table top;
(f) a second mast;
(g) means for coupling said second mast for translational movement with respect to said base such that said second mast movement is independent from and not in response to said movement of said table top;
(h) means for coupling an x-ray source to said first mast for movement with respect to said first mast, and
(i) means for coupling an image receptor to said second mast for movement with respect to said second mast.

41. The system of claim 40, further comprising:
(a) said base defining track structure extending generally horizontally;
(b) said first and second masts being substantially vertically mounted for movement along said track structure;
(c) means for coupling together said first and second masts for ganged movement with said first and second masts being displaced horizontally from one another;
(d) said x-ray source coupling means and said image receptor coupling means comprise structure for vertically aligning said x-ray source and said image receptor despite horizontal displacement between said first and second masts.

42. The system of claim 40, further comprising:
(a) said x-ray source coupling means comprising structure movable from a first position supporting said source above said table top to a second position supporting said source beneath said table top independently of movement of said table top.

* * * * *